US011564872B2

(12) United States Patent
Aubrun et al.

(10) Patent No.: US 11,564,872 B2
(45) Date of Patent: Jan. 31, 2023

(54) O/W EMULSION COMPRISING A $C_{16}$—$C_{30}$ FATTY ALCOHOL, AN ANIONIC SURFACTANT, AN OIL, A WAX AND A HYDROPHILIC SOLVENT

(71) Applicant: L'OREAL, Paris (FR)

(72) Inventors: Odile Aubrun, Chevilly la Rue (FR); Arno Wahler, Chevilly la Rue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/469,508

(22) PCT Filed: Dec. 12, 2017

(86) PCT No.: PCT/EP2017/082370
§ 371 (c)(1),
(2) Date: Jun. 13, 2019

(87) PCT Pub. No.: WO2018/108878
PCT Pub. Date: Jun. 21, 2018

(65) Prior Publication Data
US 2020/0038296 A1 Feb. 6, 2020

(30) Foreign Application Priority Data
Dec. 16, 2016 (FR) ...................................... 1662653

(51) Int. Cl.
| | | |
|---|---|---|
| *A61K 8/06* | (2006.01) | |
| *A61K 8/34* | (2006.01) | |
| *A61K 8/46* | (2006.01) | |
| *A61K 8/92* | (2006.01) | |
| *A61Q 1/00* | (2006.01) | |

(52) U.S. Cl.
CPC .............. *A61K 8/062* (2013.01); *A61K 8/342* (2013.01); *A61K 8/466* (2013.01); *A61K 8/92* (2013.01); *A61Q 1/00* (2013.01)

(58) Field of Classification Search
CPC ... A61K 8/00; A61K 8/02; A61K 8/06; A61K 8/062; A61K 8/18; A61K 8/25; A61K 8/31; A61K 8/34; A61K 8/36
See application file for complete search history.

(56) References Cited

U.S. PATENT DOCUMENTS

| 2013/0005835 | A1* | 1/2013 | Uyama | ................. | A61Q 19/00 514/784 |
|---|---|---|---|---|---|
| 2015/0098973 | A1 | 4/2015 | Brissette et al. | | |
| 2015/0335471 | A1* | 11/2015 | Nakashima | ............ | A61K 47/32 607/112 |

FOREIGN PATENT DOCUMENTS

| EP | 1 086 683 A1 | 3/2001 | | |
|---|---|---|---|---|
| EP | 1 116 483 A1 | 7/2001 | | |
| EP | 2 248 513 A1 | 11/2010 | | |
| EP | 2 452 668 A1 | 5/2012 | | |
| EP | 2 494 952 A1 | 9/2012 | | |
| EP | 2 548 549 A1 | 1/2013 | | |
| JP | 5-17710 A | 1/1993 | | |
| JP | 7-258460 A | 10/1995 | | |
| JP | 9-188830 A | 7/1997 | | |
| JP | 10-158450 A | 6/1998 | | |
| JP | 10-158541 A | 6/1998 | | |
| WO | WO 2008/155059 A2 | 12/2008 | | |
| WO | WO 2013/169506 A2 | 11/2013 | | |
| WO | WO-2013169506 A2 * | 11/2013 | ........... | A61K 8/0241 |

OTHER PUBLICATIONS

International Search Report dated Feb. 26, 2018 in PCT/EP2017/082370 filed Dec. 12, 2017.
Preliminary French Search Report dated Apr. 13, 2017 in French Application 16 62653 filed on Dec. 16, 2016.
Mintel, "Medicated Vitalizing Cream," Feb. 2016, pp. 1-6, XP002769187.
Mintel, "Eye Cream," Jun. 2014, pp. 1-5, XP002769188.
Mintel database, Record ID: 3638739; Activating Cream, published in Jan. 2016.
Notice of Opposition dated Aug. 5, 2021 in an opposition proceeding in EP Application No. 17825779.6.

* cited by examiner

*Primary Examiner* — Micah Paul Young
(74) *Attorney, Agent, or Firm* — Oblon, McClelland, Maier & Neustadt, L.L.P.

(57) ABSTRACT

The present invention relates to a cosmetic composition in the form of an oil-in-water emulsion comprising: (i) at least one $C_{16}$-$C_{30}$ fatty alcohol; (ii) at least one anionic surfactant of general formula (I): $RCOY(CH_2)nSO_3M$; (iii) at least one oil; (iv) at least one wax, and (v) at least one hydrophilic solvent, the weight ratio of anionic surfactant(s) of general formula (I)/fatty alcohol(s) ranging from 1/5 to 1/3, said composition comprising from 1% to 10% by weight of wax(es) relative to the total weight of the composition. The present invention also relates to a process for preparing said composition and a cosmetic makeup and/or care process.

11 Claims, No Drawings

O/W EMULSION COMPRISING A $C_{16}$–$C_{30}$ FATTY ALCOHOL, AN ANIONIC SURFACTANT, AN OIL, A WAX AND A HYDROPHILIC SOLVENT

The present invention aims to propose, for the field of caring for and/or making up keratin materials, a most particularly beneficial presentation form in terms of its technical performance, especially in terms of conveying active agents and the sensory feelings it provides to the user during the application thereof to said keratin materials.

The term "keratin materials" especially means the skin, the lips and/or the eyelashes, in particular the skin and/or the lips, and preferably the skin.

Cosmetic compositions are commonly employed for hiding and/or unifying skin relief imperfections such as pores, wrinkles and/or fine lines and/or scars. In this regard, many solid or fluid, anhydrous or non-anhydrous formulations have been developed to date.

When these compositions are more particularly intended for blurring the visibility of the skin relief, the formulator uses therein diffusing fillers or else fillers referred to as "soft-focus fillers". However, the currently available compositions do not always prove satisfactory, especially in terms of blurring performance and may also pose sensory problems, especially a rough feel and/or a phenomenon of pilling on application.

There is thus still a need for blurring cosmetic compositions which make it possible to mask skin imperfections, which have good cosmetic properties, in particular which are non-tacky, fresh and light on application.

The present invention is specifically directed towards meeting this need.

Thus, the present invention describes a composition, especially a cosmetic composition and in particular a composition for making up and/or caring for keratin materials, in the form of an oil-in-water emulsion comprising:
  at least one $C_{16}$-$C_{30}$ fatty alcohol,
  at least one anionic surfactant of general formula (I): $RCOY(CH_2)_nSO_3M$ in which R represents a saturated, linear or branched $C_{16\text{-}22}$ alkyl group; Y represents —O— or —$NR_1$— with $R_1$ representing a linear or branched $C_{1\text{-}3}$ alkyl group; M is chosen from the group formed of hydrogen, alkali metals, alkaline earth metals, the ammonium group and organic amines; n is an integer ranging from 1 to 3;
  at least one oil,
  at least one wax, and
  at least one hydrophilic solvent chosen from the group formed of water and $C_1$-$C_5$ compounds comprising at least one OH group, said hydrophilic solvent preferably being water.

According to one aspect thereof, the present invention relates to a composition, especially a cosmetic composition and in particular a composition for making up and/or caring for keratin materials, in the form of an oil-in-water emulsion comprising:
  at least one $C_{16}$-$C_{30}$ fatty alcohol,
  at least one anionic surfactant of general formula (I): $RCOY(CH_2)_nSO_3M$ in which R represents a saturated, linear or branched $C_{16\text{-}22}$ alkyl group; Y represents —O— or —$NR_1$— with $R_1$ representing a linear or branched $C_{1\text{-}3}$ alkyl group; M is chosen from the group formed of hydrogen, alkali metals, alkaline earth metals, the ammonium group and organic amines; n is an integer ranging from 1 to 3;
  at least one oil,
  at least one wax, and
  at least one hydrophilic solvent chosen from the group formed of water and $C_1$-$C_5$ compounds comprising at least one OH group, said hydrophilic solvent preferably being water,
  the weight ratio of anionic surfactant(s) of general formula (I)/fatty alcohol(s) ranging from 1/5 to 1/3,
  said composition comprising from 1% to 10% by weight of one or more wax(es) relative to the total weight of the composition.

The composition according to the present invention advantageously makes it possible to convey ingredients varied in nature, such as cosmetic active agents, sunscreens, particles, or polymers, as a function of the different desired benefit(s).

The composition according to the present invention is also distinguished by its stability, especially by the fact that no phase excess, nor phase separation, is observed over time, and by its sensory qualities: it is non-tacky, provides a fresh feel without a wet effect, and an effect of immediate drying.

As shown in the examples below, the inventors have observed that the compositions according to the invention have a blurring effect, also referred to as a "soft focus" effect, which is particularly pronounced. Once they are spread on the skin, the compositions according to the present invention generate a more matte appearance than the initial appearance of said skin.

In addition, the sensation of discomfort which may be generated by compositions comprising soft-focus fillers is not felt upon application of the compositions according to the present invention.

The composition according to the invention also proves easy to apply to the surface of the targeted keratin material.

Patent applications US2013/0005835 A1 and EP1116483A1 relate to emulsions comprising a fatty alcohol, an anionic surfactant, water and a fatty phase. However, US2013/0005835 does not provide for the use of a wax and EP1116483A1 does not disclose the use of an anionic surfactant of formula (I) such as that used within the context of the present invention. In addition, these applications do not target obtaining a composition with a soft-focus effect.

The present invention further targets a process for preparing the composition according to the present invention, wherein the following steps are carried out:
  preparation of the fatty phase by mixing especially at least one $C_{16}$-$C_{30}$ fatty alcohol, at least one anionic surfactant of general formula (I), at least one wax, at least one oil, said mixing being carried out at a temperature ranging from 50 to 100° C.
  incorporation of at least one hydrophilic solvent, with stirring, at a temperature ranging from 50 to 100° C.

According to another aspect, the present invention relates to a cosmetic process for making up and/or caring for keratin materials, in particular the skin, especially facial skin and/or the lips, comprising at least one step consisting in applying, to said keratin material, a composition according to the invention.

Other embodiments, properties and advantages of the compositions according to the invention will emerge upon reading the following description and examples. These examples and description are not, however, to be in any way interpreted as limiting.

As indicated above, according to the present invention, the weight ratio of anionic surfactant(s) of general formula (I)/fatty alcohol(s) ranges from 1/5 (=0.2) to 1/3 (=0.33) and is advantageously approximately 1/4 (approximately 0.25).

According to a preferred variant, the mixture of anionic surfactant(s) of general formula (I) and fatty alcohol(s) represents from 1 to 40% by weight relative to the weight of the hydrophilic phase.

According to another preferred variant, the weight ratio of anionic surfactant(s) of general formula (I)/fatty alcohol(s) ranges from 1/5 to 1/3 and advantageously approximately 1/4 and the mixture of the anionic surfactant(s) of general formula (I) and fatty alcohol(s) represents from 1 to 40% by weight relative to the weight of the hydrophilic phase.

Fatty Alcohols

Advantageously, the fatty alcohol is chosen from $C_{16}$-$C_{22}$ fatty alcohols, preferably from $C_{16}$-$C_{18}$ fatty alcohols.

The fatty alcohols of use according to the present invention are especially the alcohols chosen from cetyl or hexadecanol ($C_{16}$), stearyl or octadecanol ($C_{18}$), or behenyl ($C_{22}$) alcohols, which are solid at room temperature and advantageously have a chain-end —OH group.

Use will particularly preferably be made of an alcohol chosen from cetyl, stearyl and cetylstearyl alcohols.

Preferably, the composition according to the invention comprises a mixture of $C_{16}$ and $C_{18}$ fatty alcohols, in particular the composition comprises cetylstearyl alcohol.

More preferably, the mixture of $C_{16}$ and $C_{18}$ fatty alcohols is used in a $C_{16}/C_{18}$ weight ratio ranging from 20/80 to 80/20 and advantageously in a $C_{16}/C_{18}$ weight ratio equal to 50/50.

The composition according to the invention advantageously comprises from 0.1 to 40%, preferably from 1 to 10% and preferably from 5 to 6% by weight of one or more fatty alcohol(s) relative to the total weight of the composition.

Anionic Surfactant

Preferably, the anionic surfactant of general formula (I) is N-stearoyl-N-methyltaurate, where M is chosen from H or Na.

The composition according to the invention advantageously comprises from 0.05 to 5%, preferably from 0.1 to 2% by weight of one or more anionic surfactant(s) of general formula (I) relative to the total weight of the composition.

According to a particular variant, the composition comprises from 5 to 6% by weight of cetylstearyl alcohol in a $C_{16}/C_{18}$ ratio equal to 50/50 and from 0.1 to 2% by weight of sodium N-stearoyl-N-methyltaurate relative to the total weight of the composition.

Without wishing to be bound by any theory, it appears that the fatty alcohol(s) and the anionic surfactant(s) of general formula (I) form, with the hydrophilic phase, an alpha crystalline phase, also referred to as alpha gel. This phase may especially be characterized by X-ray diffraction at a temperature lower than the melting point of the alpha phase gel.

Measuring the Soft-Focus Effect

As already mentioned, the compositions according to the present invention have a blurring effect, also referred to as a "soft-focus" effect, which is particularly pronounced.

The haze value quantifies the perception of visual effects with objective measurements. It measures the intensity of the light passing through a sample, which corresponds to the total (or hemispherical) transmittance, denoted TH. The higher the transmittance of a material, the more said material has a transparent character.

The haze value distinctly measures the direct transmittance (that is to say in the same direction as the incident ray) or the total transmittance (that is to say in all spatial directions). The more the transmittance of a material is of total or hemispherical type relative to direct transmittance, the more said material has a soft-focus effect.

The soft-focus effect is characterized by haze and transparency measurements (transmittance TH). "Haze" corresponds to the percentage of light scattered relative to the total transmittance according to standard ASTM D 1003 (Standard Test Method for Haze and Luminous Transmittance of Transparent Plastics).

$$\text{Haze (\%)} = 100 \times (TH - TD)/TH$$

25 μm films of composition to be tested are applied onto 50 μm polyethylene (PE) films. The film is then measured after 1 hour of drying at room temperature. Finally, the film is placed in the machine and transparency and haze measurements are taken.

According to one embodiment of the invention, the compositions according to the present invention have a haze value greater than or equal to 80% and a direct transmittance greater than or equal to 80%.

Of course, as indicated below, the compositions according to the invention may in parallel also contain additional conventional fillers, it being understood that those skilled in the art will take care to ensure that they do not choose fillers whose nature or amount in the composition would impair the soft-focus effect.

Oily Phase

The composition according to the invention comprises at least one oil.

The term "oil" means any fatty substance that is in liquid form at room temperature and atmospheric pressure.

Advantageously, the oil is chosen from alkanes, esters, ethers, triglycerides, silicone oils and mixtures thereof.

The oils used in the present invention are different from the $C_{16}$-$C_{30}$ fatty alcohols used in the compositions according to the invention.

An oily phase that is suitable for preparing the cosmetic compositions according to the invention may comprise hydrocarbon-based oils, silicone oils, fluoro oils or non-fluoro oils, or mixtures thereof.

The oils can be volatile or non-volatile.

They can be of animal, vegetable, mineral or synthetic origin. According to one variant embodiment, oils of plant origin are preferred.

For the purposes of the present invention, the term "non-volatile oil" means an oil with a vapor pressure of less than 0.13 Pa.

For the purposes of the present invention, the term "silicone oil" means an oil comprising at least one silicon atom, and especially at least one Si—O group.

The term "fluoro oil" means an oil comprising at least one fluorine atom.

The term "hydrocarbon-based oil" means an oil mainly containing hydrogen and carbon atoms.

The oils can optionally comprise oxygen, nitrogen, sulfur and/or phosphorus atoms, for example in the form of hydroxyl or acid radicals.

For the purposes of the invention, the term "volatile oil" means any oil that is capable of evaporating on contact with the skin in less than one hour, at room temperature and atmospheric pressure. The volatile oil is a volatile cosmetic compound, which is liquid at room temperature, especially having a non-zero vapor pressure, at room temperature and atmospheric pressure, especially having a vapor pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

Volatile Oils

The volatile oils can be hydrocarbon-based oils or silicone oils.

Among the volatile hydrocarbon-based oils having from 8 to 16 carbon atoms, mention may be made especially of branched $C_8$-$C_{16}$ alkanes, such as $C_8$-$C_{16}$ isoalkanes (also referred to as isoparaffins), isododecane, isodecane, isohexadecane and, for example, the oils sold under the trade names Isopar or Permethyl, branched $C_8$-$C_{16}$ esters, such as isohexyl neopentanoate, and mixtures thereof. Preferably, the volatile hydrocarbon-based oil is chosen from volatile hydrocarbon-based oils having from 8 to 16 carbon atoms, and mixtures thereof, in particular from isododecane, isodecane and isohexadecane, and is especially isohexadecane.

Mention may also be made of volatile linear alkanes comprising from 8 to 16 carbon atoms, in particular from 10 to 15 carbon atoms and more particularly from 11 to 13 carbon atoms, for example such as n-dodecane ($C_{12}$) and n-tetradecane ($C_{14}$) sold by Sasol under the respective references PARAFOL 12-97 and PARAFOL 14-97, and also mixtures thereof, the undecane-tridecane mixture, mixtures of n-undecane ($C_{11}$) and of n-tridecane ($C_{13}$) obtained in examples 1 and 2 of patent application WO 2008/155 059 from Cognis, and mixtures thereof.

Mention may be made, as volatile silicone oils, of linear volatile silicone oils, such as hexamethyldisiloxane, octamethyltrisiloxane, decamethyltetrasiloxane, tetradecamethylhexasiloxane, hexadecamethylheptasiloxane and dodecamethylpentasiloxane.

Mention may be made, as volatile cyclic silicone oils, of hexamethylcyclotrisiloxane, octamethylcyclotetrasiloxane, decamethylcyclopentasiloxane and dodecamethylcyclohexasiloxane.

Non-Volatile Oils

The non-volatile oils may especially be chosen from non-volatile hydrocarbon-based, fluoro and/or silicone oils.

Mention may especially be made, as non-volatile hydrocarbon-based oil, of:
  hydrocarbon-based oils of animal origin,
  hydrocarbon-based oils of plant origin, synthetic ethers having from 10 to 40 carbon atoms, such as dicaprylyl ether,
  synthetic esters, such as oils of formula $R_1COOR_2$, in which $R_1$ represents a residue of a linear or branched fatty acid comprising from 1 to 40 carbon atoms and $R_2$ represents a hydrocarbon-based chain, especially a branched hydrocarbon-based chain, containing from 1 to 40 carbon atoms, provided that $R_1+R_2$ is $\geq 10$. The esters may especially be chosen from esters of alcohol and of fatty acid, such as, for example, cetostearyl octanoate, esters of isopropyl alcohol, such as isopropyl myristate or isopropyl palmitate, ethyl palmitate, 2-ethylhexyl palmitate, isopropyl stearate, octyl stearate, hydroxylated esters, such as isostearyl lactate or octyl hydroxystearate, alkyl or polyalkyl ricinoleates, hexyl laurate, esters of neopentanoic acid, such as isodecyl neopentanoate or isotridecyl neopentanoate, or esters of isononanoic acid, such as isononyl isononanoate or isotridecyl isononanoate,
  polyol esters and pentaerythritol esters, such as dipentaerythrityl tetrahydroxystearate/tetraisostearate,
  fatty alcohols that are liquid at room temperature, bearing a branched and/or unsaturated carbon-based chain having from 12 to 26 carbon atoms, such as 2-octyldodecanol, isostearyl alcohol and oleyl alcohol,
  higher $C_{12}$-$C_{22}$ fatty acids, such as oleic acid, linoleic acid and linolenic acid, and mixtures thereof,
  branched or unbranched, in particular saturated, $C_7$-$C_{40}$ fatty acid triglycerides, such as caprylic/capric acid triglycerides and mixtures thereof, and $C_{10\text{-}36}$ acid triglycerides,
  nonphenylated silicone oils, such as, for example, caprylyl methicone, and
  phenylated silicone oils, such as, for example, phenyl trimethicones, phenyl dimethicones, phenyl(trimethylsiloxy)diphenylsiloxanes, diphenyl dimethicones, diphenyl(methyldiphenyl)trisiloxanes and (2-phenylethyl)trimethylsiloxysilicates, dimethicones or phenyl trimethicones with a viscosity of less than or equal to 100 cSt, trimethylpentaphenyltrisiloxane, and mixtures thereof; and also the mixtures of these different oils.

A composition according to the invention may comprise from 0.01% to 80%, preferably from 0.1 to 40% and advantageously from 2% to 10% by weight of one or more oil(s) relative to the total weight of the composition.

Waxes

The composition according to the invention comprises at least one wax.

The Waxes

A "wax" is a lipophilic substance in the form of a branched or unbranched, saturated or unsaturated alkane or ester of fatty acid and fatty alcohol.

The term "wax" under consideration in the context of the present invention generally means a lipophilic compound that is solid at room temperature (25° C.), with a solid/liquid reversible change of state, having a melting point of greater than or equal to 30° C., which may be up to 200° C. and especially up to 120° C.

The waxes used in the present invention are different from the $C_{16}$-$C_{30}$ fatty alcohols used in the compositions according to the invention and different from the oils used in the compositions according to the invention.

For the purposes of the invention, the melting point corresponds to the temperature of the most endothermic peak observed on thermal analysis (DSC) as described in standard ISO 11357-3; 1999. The melting point of the wax may be measured using a differential scanning calorimeter (DSC), for example the calorimeter sold under the name MDSC 2920 by the company TA Instruments.

The measurement protocol is as follows:

A 5 mg sample of wax placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes that may be used in the compositions according to the invention are chosen from waxes that are solid at room temperature, of animal, plant, mineral or synthetic origin, and mixtures thereof.

The waxes, for the purposes of the invention, may be those generally used in the cosmetic or dermatological fields. They may especially be polar or apolar, hydrocarbon-based, silicone and/or fluoro waxes, optionally comprising ester or hydroxyl functions. They may also be of natural or synthetic origin.

Advantageously, the wax is chosen from paraffins, esters, triglycerides, silicone waxes and mixtures thereof.

a) Apolar Waxes

For the purposes of the present invention, the term "apolar wax" means a wax of which the solubility parameter at 25° C. as defined below, $\delta_a$, is equal to 0 $(J/cm^3)^{1/2}$.

The definition and calculation of the solubility parameters in the Hansen three-dimensional solubility space are described in the article by C. M. Hansen: "*The three dimensional solubility parameters*" J. Paint Technol. 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the forces of specific interactions (such as hydrogen bonds, acid/base bonds, donor/acceptor bonds, and the like);

$\delta_a$ is determined by the equation: $\delta_a=(\delta_p^2+\delta_h^2)^{1/2}$.

The parameters $\delta_p$, $\delta_h$, $\delta_D$ and $\delta_a$ are expressed as $(J/cm^3)^{1/2}$.

The apolar waxes are in particular hydrocarbon-based waxes formed solely from carbon and hydrogen atoms, and free of heteroatoms such as N, O, Si and P.

The apolar waxes are chosen from microcrystalline waxes, paraffin waxes, ozokerite and polyethylene waxes, and mixtures thereof.

An ozokerite that may be mentioned is Ozokerite Wax SP 1020 P.

As microcrystalline waxes that may be used, mention may be made of Multiwax W 445® sold by Sonneborn, and Microwax HW® and Base Wax 30540® sold by Paramelt, and Cerewax® No. 3 sold by Baerlocher.

As microwaxes that may be used in the compositions according to the invention as apolar wax, mention may be made especially of polyethylene microwaxes such as those sold under the names Micropoly 200®, 220®, 220L® and 250S® by Micro Powders.

Polyethylene waxes that may be mentioned include Performalene 500-L Polyethylene and Performalene 400 Polyethylene sold by New Phase Technologies, and Asensa® SC 211 sold by Honeywell.

b) Polar Wax

For the purposes of the present invention, the term "polar wax" means a wax whose solubility parameter at 25° C., δa, is other than 0 $(J/cm^3)^{1/2}$.

In particular, the term "polar wax" means a wax whose chemical structure is formed essentially from, or even constituted by, carbon and hydrogen atoms, and comprising at least one highly electronegative heteroatom such as an oxygen, nitrogen, silicon or phosphorus atom.

The polar waxes may be especially be hydrocarbon-based, fluoro or silicone waxes.

Preferentially, the polar waxes may be hydrocarbon-based waxes.

The term "hydrocarbon-based wax" means a wax formed essentially from, or even constituted by, carbon and hydrogen atoms, and optionally oxygen and nitrogen atoms, and that does not contain any silicon or fluorine atoms. It may contain alcohol, ester, ether, carboxylic acid, amine and/or amide groups.

The term "ester wax" means, according to the invention, a wax comprising at least one ester function. The term "alcohol wax" means, according to the invention, a wax comprising at least one alcohol function, that is to say comprising at least one free hydroxyl (OH) group.

Use may especially be made, as ester wax, of:

ester waxes, such as those chosen from:
i) waxes of formula $R_1COOR_2$ in which $R_1$ and $R_2$ represent linear, branched or cyclic aliphatic chains in which the number of atoms ranges from 10 to 50, which may contain a heteroatom such as O, N or P and whose melting point ranges from 25 to 120° C.;
ii) bis(1,1,1-trimethylolpropane) tetrastearate, sold under the name Hest 2T-4S® by Heterene;
iii) diester waxes of a dicarboxylic acid of general formula $R^3$—(—OCO—$R^4$—COO—$R^5$), in which $R^3$ and $R^5$ are identical or different, preferably identical, and represent a $C_4$-$C_{30}$ alkyl group (alkyl group comprising from 4 to 30 carbon atoms) and $R^4$ represents a linear or branched $C_4$-$C_{30}$ aliphatic group (alkyl group comprising from 4 to 30 carbon atoms) which may or may not comprise one or more unsaturation(s) and which is preferably linear and unsaturated;
iv) mention may also be made of the waxes obtained by catalytic hydrogenation of animal or vegetable oils having linear or branched $C_8$-$C_{32}$ fatty chains, for example such as hydrogenated jojoba oil, hydrogenated sunflower oil, hydrogenated castor oil, hydrogenated coconut oil, and also the waxes obtained by hydrogenation of castor oil esterified with cetyl alcohol;
v) beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumac wax, montan wax, orange wax, laurel wax, hydrogenated jojoba wax, sunflower wax, lemon wax, olive wax or berry wax.

According to another embodiment, the polar wax can be an alcohol wax. The term "alcohol wax" means, according to the invention, a wax comprising at least one alcohol function, that is to say comprising at least one free hydroxyl (OH) group. Examples of alcohol waxes that may be mentioned include the $C_{30}$-$C_{50}$ alcohol wax Performacol® 550 Alcohol sold by New Phase Technologies, stearyl alcohol and cetyl alcohol.

It is also possible to use silicone waxes, which may advantageously be substituted polysiloxanes, preferably of low melting point.

The term "silicone wax" means an oil comprising at least one silicon atom and especially comprising Si—O groups.

Among the commercial silicone waxes of this type, mention may be made in particular of those sold under the names Abilwax 9800, 9801 or 9810 (Goldschmidt), KF910 and KF7002 (Shin-Etsu), or 176-1118-3 and 176-11481 (General Electric).

The silicone waxes of use may also be alkyl or alkoxy dimethicones, and also ($C_{20}$-$C_{60}$)alkyl dimethicones, in particular ($C_{30}$-$C_{45}$)alkyl dimethicones, such as the silicone wax sold under the name SF-1642 by GE-Bayer Silicones or $C_{30-45}$ alkyl dimethylsilyl polypropylsilsesquioxane under the name SW-8005® C30 Resin Wax sold by Dow Corning.

In the context of the present invention, particularly advantageous waxes that may be mentioned include polyethylene waxes, jojoba wax, candelilla wax and silicone waxes, in particular candelilla wax.

As indicated above, the composition according to the present invention comprises from 1% to 10% by weight of one or more waxes relative to the total weight of the composition, preferably 1%, 2%, 3%, 4%, 5%, 6%, 7%, 8%, 9% or 10% by weight of one or more waxes relative to the total weight of the composition.

In particular, the fatty phase (comprising $C_{16}$-$C_{30}$ fatty alcohols, oils and waxes) of the composition according to the present invention ranges from 1% to 80% by weight relative to the total weight of the composition.

Hydrophilic Phase

As already mentioned, the composition according to the invention comprises at least one hydrophilic solvent chosen from the group formed of water and $C_1$-$C_5$ compounds comprising at least one OH group, said hydrophilic solvent preferably being water.

The hydrophilic phase may advantageously comprise water and at least one $C_1$-$C_5$ compound comprising at least one OH group.

In the present invention, the term "hydrophilic solvent", other than water, denotes a compound that is liquid at room temperature and water-miscible (miscibility with water of greater than 50% by weight at 25° C. and atmospheric pressure).

Among the $C_1$-$C_5$ hydrophilic solvents which may be used in the composition in accordance with the invention, mention may especially be made of:
  lower monoalcohols having from 1 to 5 carbon atoms, such as ethanol and isopropanol;
  glycols having from 2 to 5 carbon atoms such as ethylene glycol, propylene glycol, 1,3-butylene glycol and dipropylene glycol;
  $C_2$-$C_5$ polyols and more particularly ethylene glycol, pentaerythritol, propylene glycol, 1,3-propanediol, butylene glycol, isoprene glycol.

The hydrophilic phase may also comprise at least one glycol having from 6 to 8 carbon atoms and also at least one compound chosen from $C_3$ and $C_4$ ketones and $C_2$-$C_4$ aldehydes.

The hydrophilic phase may also comprise at least one $C_6$-$C_{32}$ polyol.

For the purposes of the present invention, the term "polyol" should be understood as meaning any organic molecule comprising at least two free hydroxyl groups.

Preferably, a polyol in accordance with the present invention is present in liquid form at room temperature.

A polyol that is suitable for use in the invention may be a compound of linear, branched or cyclic, saturated or unsaturated alkyl type, bearing on the alkyl chain at least two —OH functions, in particular at least three —OH functions and more particularly at least four —OH functions.

Colorants

A composition according to the invention may also comprise at least one particulate or non-particulate, water-soluble or water-insoluble colorant, preferably in a proportion of at least 0.01% by weight relative to the total weight of the composition.

For obvious reasons, this amount is liable to vary significantly with regard to the intensity of the desired color effect and of the color intensity afforded by the colorants under consideration, and its adjustment clearly falls within the competence of those skilled in the art.

A composition according to the invention may comprise from 0.01% to 25% by weight, especially from 0.1% to 25% by weight, in particular from 1% to 20% by weight and preferably from 2.5% to 15% by weight of colorants relative to the total weight of said composition.

As specified above, the colorants that are suitable for use in the invention may be water-soluble, but may also be liposoluble.

For the purposes of the invention, the term "water-soluble colorant" means any natural or synthetic, generally organic compound, which is soluble in an aqueous phase or water-miscible solvents and which is capable of imparting color.

As water-soluble dyes that are suitable for use in the invention, mention may be made especially of synthetic or natural water-soluble dyes, for instance FDC Red 4, DC Red 6, DC Red 22, DC Red 28, DC Red 30, DC Red 33, DC Orange 4, DC Yellow 5, DC Yellow 6, DC Yellow 8, FDC Green 3, DC Green 5, FDC Blue 1, betanine (beetroot), carmine, copper chlorophylline, methylene blue, anthocyanins (enocianin, black carrot, hibiscus and elder), caramel and riboflavin.

The water-soluble dyes are, for example, beetroot juice and caramel.

For the purposes of the invention, the term "liposoluble colorant" means any natural or synthetic, generally organic compound, which is soluble in an oily phase or in solvents that are miscible with a fatty substance, and which is capable of imparting color.

As liposoluble dyes that are suitable for use in the invention, mention may be made especially of synthetic or natural liposoluble dyes, for instance DC Red 17, DC Red 21, DC Red 27, DC Green 6, DC Yellow 11, DC Violet 2, DC Orange 5, Sudan red, carotenes (β-carotene, lycopene), xanthophylls (capsanthin, capsorubin, lutein), palm oil, Sudan brown, quinoline yellow, annatto and curcumin.

These coloring particulate materials may be present in a proportion of from 0.01% to 15% by weight relative to the total weight of the composition containing them.

They may especially be pigments, nacres and/or particles with metallic glints.

The term "pigments" should be understood as meaning white or colored, mineral or organic particles that are insoluble in a hydrophilic solution, especially an aqueous hydrophilic solution, and which are intended to color and/or opacify the composition containing them.

A composition according to the invention may comprise from 0.01% to 25% by weight, especially from 0.1% to 25% by weight, in particular from 1% to 25% by weight and preferably from 2.5% to 15% by weight of pigments relative to the total weight of said composition.

Preferably, when the composition according to the invention is a makeup composition, it may comprise at least 2.5% and preferentially at least 10% by weight of pigments relative to the total weight of said composition.

The pigments may be white or colored, and mineral and/or organic.

As mineral pigments of use in the invention, mention may be made of titanium oxide, titanium dioxide, zirconium oxide, zirconium dioxide, cerium oxide or cerium dioxide and also zinc oxide, iron oxide or chromium oxide, ferric blue, manganese violet, ultramarine blue and chromium hydrate, and mixtures thereof.

They may also be a pigment having a structure that may be, for example, of sericite/brown iron oxide/titanium dioxide/silica type. Such a pigment is sold, for example, under the reference Coverleaf NS or JS by Chemicals and Catalysts, and has a contrast ratio in the region of 30.

They may also be pigments having a structure that may be, for example, of silica microsphere type containing iron oxide. An example of a pigment having this structure is that sold by Miyoshi under the reference PC Ball PC-LL-100 P, this pigment being constituted of silica microspheres containing yellow iron oxide.

Advantageously, the pigments in accordance with the invention are iron oxides and/or titanium dioxides.

The term "nacres" should be understood as meaning iridescent or non-iridescent colored particles of any shape, especially produced by certain molluscs in their shell or alternatively synthesized, which have a color effect via optical interference.

A composition according to the invention may comprise from 0% to 15% by weight of nacres relative to the total weight of said composition.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles, at the surface of which are superposed at least two successive layers of metal oxides and/or of organic colorants.

Examples of nacres that may also be mentioned include natural mica coated with titanium oxide, with iron oxide, with natural pigment or with bismuth oxychloride.

Among the nacres available on the market, mention may be made of the nacres Timica, Flamenco and Duochrome (based on mica) sold by Engelhard, the Timiron nacres sold by Merck, the Prestige mica-based nacres sold by Eckart, and the Sunshine synthetic mica-based nacres sold by Sun Chemical.

The nacres may more particularly have a yellow, pink, red, bronze, orangey, brown, gold and/or coppery color or glint.

Advantageously, the nacres in accordance with the invention are micas coated with titanium dioxide or with iron oxide, and also bismuth oxychloride.

For the purposes of the present invention, the term "particles with a metallic glint" means any compound whose nature, size, structure and surface finish allow it to reflect the incident light, especially in a non-iridescent manner.

The particles with a metallic glint that may be used in the invention are in particular chosen from:
  particles of at least one metal and/or of at least one metal derivative;
  particles comprising a monomaterial or multimaterial organic or mineral substrate, at least partially coated with at least one layer with a metallic glint comprising at least one metal and/or at least one metal derivative; and
  mixtures of said particles.

Among the metals that may be present in said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr, and mixtures or alloys thereof (for example bronzes and brasses) are preferred metals.

The term "metal derivatives" denotes compounds derived from metals, especially oxides, fluorides, chlorides and sulfides.

Illustrations of these particles that may be mentioned include aluminum particles, such as those sold under the names Starbrite 1200 EAC® by Siberline and Metalure® by Eckart and glass particles coated with a metallic layer, especially those described in documents JP-A-09188830, JP-A-10158450, JP-A-10158541, JP-A-07258460 and JP-A-05017710.

Hydrophobic Treatment of the Colorants

The pulverulent colorants as described previously may be totally or partially surface-treated, with a hydrophobic agent, to make them more compatible with the oily phase of the composition of the invention, especially so that they have good wettability with oils. Thus, these treated pigments are well dispersed in the oily phase.

Hydrophobic-treated pigments are described especially in document EP-A-1 086 683.

The hydrophobic-treatment agent may be chosen from silicones such as methicones, dimethicones and perfluoroalkylsilanes; fatty acids, such as stearic acid; metal soaps, such as aluminum dimyristate, the aluminum salt of hydrogenated tallow glutamate; perfluoroalkyl phosphates; polyhexafluoropropylene oxides; perfluoropolyethers; amino acids; N-acylamino acids or salts thereof lecithin, isopropyl triisostearyl titanate, isostearyl sebacate, and mixtures thereof.

The term "alkyl" mentioned in the compounds cited above especially denotes an alkyl group having from 1 to 30 carbon atoms and preferably having from 5 to 16 carbon atoms.

Additional Fillers

Advantageously, a composition according to the invention may comprise one or more filler(s) conventionally used in care and/or makeup compositions.

These additional fillers are colorless or white solid particles of any form, which are in a form that is insoluble and dispersed in the medium of the composition.

These fillers, of mineral or organic, natural or synthetic nature, give the composition containing them softness and give the makeup result a matt effect and uniformity.

In particular, such additional fillers may be present in a composition according to the invention in a content of between 0.5% and 10% by weight, especially between 0.5% and 7% by weight and in particular between 0.5% and 5% by weight relative to the total weight of the composition.

According to one embodiment of the invention, a composition may comprise at least solid particles such as pigments and/or additional fillers.

Advantageously, a composition according to the invention may comprise from 0.01% to 25% by weight, especially from 0.1% to 25% by weight, in particular from 1% to 20% by weight and preferably from 5% to 15% by weight of solid particles relative to the total weight of the composition.

UV-Screening Agents

The compositions according to the invention may also contain at least one UV-screening agent. Preferably, the UV-screening agent that is suitable for use in the invention is chosen from water-soluble UV-screening agents, liposoluble UV-screening agents, insoluble UV-screening agents, and mixtures thereof. Among these UV-screening agents, a distinction can be made between water-soluble organic screening agents, liposoluble organic screening agents, insoluble organic screening agents and inorganic screening agents.

Preferentially, the UV-screening agent(s) are chosen from water-soluble UV-screening agents, liposoluble UV-screening agents, and mixtures thereof, and even more preferably chosen from water-soluble organic UV-screening agents and liposoluble organic screening agents, and mixtures thereof, and more particularly liposoluble organic UV-screening agents.

The UV-screening agent(s) can be present in the composition in a content ranging from 0.1% to 15% by weight, especially from 0.5% to 10% by weight, relative to the total weight of said composition.

Active Agent

For a care application in particular, a composition according to the invention can comprise at least one moisturizing agent (also known as humectant).

The moisturizing agent or agents can be present in the composition in a content ranging from 0.1% to 15% by weight, especially from 0.5% to 10% by weight, or even from 1% to 6% by weight, relative to the total weight of said composition.

As other active agents of use in the composition of the invention, mention may be made, for example, of vitamins.

Preferably, a composition according to the invention comprises at least one active agent.

It is a matter of routine operation for those skilled in the art to adjust the nature and the amount of the additives present in the compositions in accordance with the invention such that the desired cosmetic properties thereof are not thereby affected.

According to one embodiment, a composition of the invention may advantageously be in the form of a composition for caring for the skin of the body or the face, in particular the face.

According to another embodiment, a composition of the invention may advantageously be in the form of a makeup base composition.

According to another embodiment, a composition of the invention may advantageously be in the form of a foundation.

According to one embodiment, a composition of the invention may advantageously be in the form of a composition for making up the skin and especially the face. It may thus be an eyeshadow or a face powder.

According to another embodiment, a composition of the invention may advantageously be in the form of a lip product, especially a lipstick.

According to another embodiment, a composition of the invention may be in the form of a product for the eyelashes, in particular a mascara.

Such compositions are especially prepared according to the general knowledge of those skilled in the art.

Throughout the description, including the claims, the term "comprising a" should be understood as being synonymous with "comprising at least one", unless otherwise specified.

The terms "between . . . and . . . " and "ranging from . . . to . . . " should be understood as being inclusive of the limits, unless otherwise specified.

The invention is illustrated in greater detail by the examples presented below. Unless otherwise indicated, the amounts shown are expressed as percentages by weight.

EXAMPLES

A) Compositions

The components of the fatty phase: fatty alcohol(s), surfactant(s) of formula (I), oil(s) and optionally wax(es) are weighed and mixed in a jacketed vessel temperature-controlled to a temperature of 80° C. with mechanical stirring controlled by means of a MiniLab® OLSA vacuum mixer; the stirring is carried out for 20 minutes.

The water, heated to 80° C., is incorporated into the fatty phase, then the mixture is emulsified by rotor-stator shearing (3500 rpm) for 10 minutes.

The heating is stopped and gradual cooling under vacuum is carried out by circulating cold water within the jacket, while maintaining the emulsifying shearing of the rotor-stator at 3000 rpm (for 15 to 30 minutes).

The emulsifying shearing is stopped when the cooling reaches 40° C.

| Compounds INCI name | Example 1 In accordance with the invention | Example 2 In accordance with the invention | Example 3 Comparative |
|---|---|---|---|
| 50/50 C16/C18 cetylstearyl alcohol sold under the name Lanette O OR by Cognis | 5.6 | 5.6 | 5.6 |
| Sodium N-stearoyl-N-methyltaurate sold under the name Nikkol SMT by Nikko | 1.4 | 1.4 | 1.4 |
| caprylic/capric acid triglycerides sold under the name Dub MCT 7030 by Stéarinerie Du Bois | 21.0 | 21.0 | 30.0 |
| stabilized paraffin waxes and hydrocarbon waxes sold under the name Sasolwax 5603 by Sasol | 9.0 | 0 | 0 |
| Hydrogenated jojoba oil sold under the name Jojoba Wax Flakes by Desert Whale | 0 | 9.0 | 0 |
| Deionized water | 63.0 | 63.0 | 63.0 |

-continued

| Compounds INCI name | Example 4 In accordance with the invention | Example 5 In accordance with the invention | Example 6 Comparative | Example 7 In accordance with the invention |
|---|---|---|---|---|
| 50/50 C16/C18 cetylstearyl alcohol sold under the name Lanette O OR by Cognis | 5.6 | 5.6 | 5.6 | 5.6 |
| Sodium N-stearoyl-N-methyltaurate sold under the name Nikkol SMT by Nikko | 1.4 | 1.4 | 1.4 | 1.4 |
| PDMS 5 cSt silicone oil sold under the name Belsil DM5 Plus by Wacker | 21.0 | 21.0 | 30.0 | 24.0 |
| stabilized paraffin waxes and hydrocarbon waxes sold under the name Sasolwax 5603 by Sasol | 9.0 | 0 | 0 | 0 |
| Hydrogenated jojoba oil sold under the name Jojoba Wax Flakes by Desert Whale | 0 | 9 | 0 | 6.0 |
| Deionized water | 63.0 | 63.0 | 63.0 | 63.0 |

B) Evaluation of the Soft-Focus Effect

The various formulas were spread at a thickness of 25 microns by means of an automatic spreader (Byko drive®) on a 50 μm polyethylene film. After a drying time of one hour at room temperature (20° C.) in the open air, optical measurements (TD, TH and lightness) are carried out via Haze Gard at three separate points on the deposit, in order to obtain a mean value.

The state of the film is also characterized visually. In order for the measurements to be relevant, the deposit must be uniform, without striations or heterogeneity.

The values of total transmittance and "haze" were evaluated.

As already described, "haze" corresponds to the percentage of light scattered relative to the total transmittance according to standard ASTM D 1003 (Standard Test Method for Haze and Luminous Transmittance of Transparent Plastics).

The results are given in the table below:

The standard deviations of the mean values for haze and transmittance are: +/−3.

| Compositions | Mean Transmittance | Mean haze value | Mean clarity value |
|---|---|---|---|
| Example 1 | 94.13 | 96.6 | 11.5 |
| Example 2 | 91.5 | 95.2 | 32.7 |
| Example 3 | 90.6 | 15.7 | 51.7 |
| Example 4 | 92.9 | 93.9 | 12.8 |

-continued

| Compositions | Mean Transmittance | Mean haze value | Mean clarity value |
|---|---|---|---|
| Example 5 | 90.0 | 97.5 | 12.8 |
| Example 6 | 90.3 | 45.4 | 25.4 |

A high "haze" reflects a substantial soft-focus effect.

The compositions according to the invention have high direct transmittance and "haze" values. Consequently, the compositions according to the invention make it possible to obtain a substantial soft-focus effect.

On the other hand, the comparative compositions have low haze values, reflecting an insufficient soft-focus effect.

For the composition of example 7, the total transmittance and "haze" values were not evaluated.

Visually, the composition of example 7 does not exhibit signs of macroscopic instabilities at room temperature at 6 months.

C) Impact of the Value of the Content by Weight of Waves Relative to the Total Weight of the Composition

C.1 Composition

Compositions 8 to 11 according to the invention and comparative compositions 12 and 13 featured in the tables below were prepared according to the protocol described above under section A).

In these compositions, the weight ratio of anionic surfactant(s) of general formula (I)/fatty alcohol(s) was set at 0.25.

| Compounds INCI name | Example 8 In accordance with the invention | Example 9 In accordance with the invention | Example 10 In accordance with the invention |
|---|---|---|---|
| 50/50 C16/C18 cetylstearyl alcohol sold under the name Lanette O OR by Cognis | 5.6 | 5.6 | 5.6 |
| Sodium N-stearoyl-N-methyltaurate sold under the name Nikkol SMT by Nikko | 1.4 | 1.4 | 1.4 |
| PDMS 5 cSt silicone oil sold under the name Belsil DM5 Plus by Wacker | 21.0 | 21.0 | 21.0 |
| Hydrogenated jojoba oil sold under the name Jojoba Wax Flakes by Desert Whale | 1.0 | 2.0 | 9.0 |
| Chlorphenesin sold under the name Macrocide-OL by Macrocare | 0.2 | 0.2 | 0.2 |
| Deionized water | 70.8 | 69.8 | 62.8 |

-continued

| Compounds INCI name | Example 11 In accordance with the invention | Example 12 Comparative | Example 13 Comparative |
|---|---|---|---|
| 50/50 C16/C18 cetylstearyl alcohol sold under the name Lanette O OR by Cognis | 5.6 | 5.60 | 5.6 |
| Sodium N-stearoyl-N-methyltaurate sold under the name Nikkol SMT by Nikko | 1.4 | 1.40 | 1.4 |
| PDMS 5 cSt silicone oil sold under the name Belsil DM5 Plus by Wacker | 21.0 | 21.00 | 21 |
| Hydrogenated jojoba oil sold under the name Jojoba Wax Flakes by Desert Whale | 10.0 | 0.25 | 20 |
| Chlorphenesin sold under the name Macrocide-OL by Macrocare | 0.2 | 0.20 | 0.2 |
| Deionized water | 61.8 | 71.55 | 51.8 |

C.2 Evaluation of the Soft-Focus Effect

This evaluation (mean transmittance, mean haze value and mean lightness value) was carried out as described in section B) above.

| Compositions | Mean Transmittance | Mean haze value | Mean clarity value |
|---|---|---|---|
| Example 8 | 92.66 | 83.46 | not evaluated |
| Example 9 | 92.53 | 85.53 | not evaluated |
| Example 10 | 92.9 | 93.9 | 12.8 |
| Example 11 | 91.33 | 93.86 | 33.8 |
| Example 12 | 92.3 | 49.26 | 42.2 |
| Example 13 | 90.66 | 38 | 87.9 |

A high "haze" reflects a substantial soft-focus effect.

The compositions according to the invention have high "haze" values.

Consequently, the compositions according to the invention (content of waxes ranging from 1% to 10% by weight relative to the total weight of the composition) make it possible to obtain a substantial soft-focus effect.

On the other hand, the comparative compositions, comprising a content of waxes of 0.25% by weight or of 20% by weight relative to the total weight of the composition, have low haze values, reflecting an insufficient soft-focus effect.

D) Impact of the Value of the Weight Ratio of Anionic Surfactant(s) of General Formula (I)/Fatty Alcohol(s)

D.1 Compositions

Compositions 10, 14 and 15 according to the invention and comparative compositions 16 and 17 featured in the tables below were prepared according to the protocol described above under section A).

In these compositions, the content of waxes was set at 9% by weight relative to the total weight of the composition.

| Compounds INCI name | Example 14 In accordance with the invention | Example 10 In accordance with the invention | Example 15 In accordance with the invention |
|---|---|---|---|
| 50/50 C16/C18 cetylstearyl alcohol sold under the name Lanette O OR by Cognis | 5.83 | 5.6 | 5.25 |
| Sodium N-stearoyl-N-methyltaurate sold under the name Nikkol SMT by Nikko | 1.17 | 1.4 | 1.75 |
| PDMS 5 cSt silicone oil sold under the name Belsil DM5 Plus by Wacker | 21.00 | 21.0 | 21.00 |
| Hydrogenated jojoba oil sold under the name Jojoba Wax Flakes by Desert Whale | 9.00 | 9.0 | 9.00 |
| Chlorphenesin sold under the name Macrocide-OL by Macrocare | 0.20 | 0.2 | 0.20 |
| Deionized water | 62.80 | 62.8 | 62.80 |
| Weight ratio of anionic surfactant(s) of general formula (I)/fatty alcohol(s) | 0.2 | 0.25 | 0.33 |

| Compounds INCI name | Example 16 Comparative | Example 17 Comparative |
|---|---|---|
| 50/50 C16/C18 cetylstearyl alcohol sold under the name Lanette O OR by Cognis | 6.67 | 2.33 |
| Sodium N-stearoyl-N-methyltaurate sold under the name Nikkol SMT by Nikko | 0.33 | 4.67 |
| PDMS 5 cSt silicone oil sold under the name Belsil DM5 Plus by Wacker | 21.00 | 21.00 |
| Hydrogenated jojoba oil sold under the name Jojoba Wax Flakes by Desert Whale | 9.00 | 9.00 |
| Chlorphenesin sold under the name Macrocide-OL by Macrocare | 0.20 | 0.20 |

-continued

| | | |
|---|---|---|
| Deionized water | 62.80 | 62.80 |
| Weight ratio of anionic surfactant(s) of general formula (I)/fatty alcohol(s) | 0.05 | 2 |

D.2 Evaluation of the Soft-Focus Effect

This evaluation (mean transmittance, mean haze value and mean lightness value) was carried out as described in section B) above.

| Compositions | Mean Transmittance | Mean haze value | Mean clarity value |
|---|---|---|---|
| Example 14 | 91.43 | 98.53 | not evaluated |
| Example 10 | 92.90 | 93.90 | 12.8 |
| Example 15 | 92.26 | 87.40 | not evaluated |
| Example 16 | 91.70 | 33.50 | 89.6 |
| Example 17 | 90.63 | 7.60 | 94.5 |

A high "haze" reflects a substantial soft-focus effect.

The compositions according to the invention have high "haze" values.

Consequently, the compositions according to the invention (weight ratio of anionic surfactant(s) of general formula (I)/fatty alcohol(s) ranging from 1/5 (=0.2) to 1/3 (=0.33) make it possible to obtain a substantial soft-focus effect.

On the other hand, the comparative compositions, comprising a weight ratio of anionic surfactant(s) of general formula (I)/fatty alcohol(s) of 0.05 or of 2, have low haze values, reflecting an insufficient soft-focus effect.

The invention claimed is:

1. A composition, in the form of an oil-in-water emulsion comprising:
   from 0.1 to 40% by weight relative to the total weight of the composition of a mixture of a $C_{16}$ and $C_{18}$ fatty alcohol,
   from 0.05 to 5% by weight relative to the total weight of the composition of at least one anionic surfactant of formula (I): $RCOY(CH_2)nSO_3M$,
   wherein R represents a saturated, linear or branched $C_{16-22}$ alkyl group;
   Y represents —O— or —$NR_1$—with $R_1$ representing a linear or branched $C_{1-3}$ alkyl group;
   M is selected from the group consisting of hydrogen, alkali metals, alkaline earth metals, the ammonium group and organic amines;
   n is an integer ranging from 1 to 3;
   from 0.01% to 40% by weight relative to the total weight of the composition of at least one oil,
   from 1% to 10% by weight relative to the total weight of the composition of at least one polar wax, and
   at least one hydrophilic solvent chosen from the group formed of water and $C_1$-$C_5$ compounds comprising at least one OH group,
   wherein
   the weight ratio of the anionic surfactant of formula (I)/fatty alcohol is from 1/5 to 1/3, and
   a mean haze value of a 25 μm in film of the composition applied onto 50 μm polyethylene (PE) film measured according to standard ASTM D 1003 after 1 hour of drying at room temperature is at least 80%.

2. The composition of claim 1, wherein the weight ratio of anionic surfactant of formula (I)/fatty alcohol is approximately 1/4.

3. The composition of claim 1, wherein the mixture of the anionic surfactant of formula (I) and fatty alcohol represents from 1 to 40% by weight relative to the weight of the hydrophilic phase.

4. The composition of claim 1, wherein a $C_{16}/C_{18}$ fatty alcohol weight ratio is from 20/80 to 80/20.

5. The composition of claim 1, wherein the anionic surfactant of formula (I) is N-stearoyl-N-methyltaurate, wherein M is H or Na.

6. The composition of claim 1, wherein the at least one oil is selected from the group consisting of alkanes, esters, ethers, triglycerides, silicone oils and mixtures thereof.

7. The composition of claim 1, wherein the at least one polar wax is selected from the group consisting of an ester wax, an alcohol wax, a silicone wax and mixtures thereof.

8. The composition of claim 1, wherein the fatty phase ranges from 0.02% to 80% by weight relative to the total weight of the composition.

9. The composition of claim 1 comprising from 5 to 6% by weight of cetylstearyl alcohol in a $C_{16}/C_{18}$ weight ratio equal to 50/50 and from 0.1 to 2% by weight of sodium N-stearoyl-N-methyltaurate relative to the total weight of the composition.

10. A process for preparing the composition of claim 1, the process comprising:
    preparing the fatty phase by mixing:
      the $C_{16}$ and $C_{18}$ fatty alcohol mixture,
      the at least one anionic surfactant of formula (I):
        $RCOY(CH_2)_nSO_3M$, wherein R represents a saturated, linear or branched $C_{16-22}$ alkyl group; Y represents —O— or —$NR_1$— with $R_1$ representing a linear or branched $C_{1-3}$ alkyl group; M is chosen from the group formed of hydrogen, alkali metals, alkaline earth metals, the ammonium group and organic amines; n is an integer ranging from 1 to 3,
      the at least one polar wax, and
      the at least one oil,
      said mixing being carried out at a temperature ranging from 50 to 100° C.; and
    incorporating the hydrophilic phase, with stirring, at a temperature ranging from 50 to 100° C.

11. A cosmetic process for making up and/or caring for keratin materials, comprising applying to said keratin material a composition in the form of an oil-in-water emulsion, the composition comprising:
    from 0.1 to 40% by weight relative to the total weight of the composition of a mixture of a $C_{16}$ and $C_{18}$ fatty alcohol,
    from 0.05 to 5% by weight relative to the total weight of the composition of at least one anionic surfactant of formula (I): $RCOY(CH_2)nSO_3M$,
    wherein R represents a saturated, linear or branched $C_{16-22}$ alkyl group;
    Y represents —O— or —$NR_1$—with $R_1$ representing a linear or branched alkyl group;
    M is selected from the group consisting of hydrogen, alkali metals, alkaline earth metals, the ammonium group and organic amines;
    n is an integer ranging from 1 to 3;

from 0.01% to 40% by weight relative to the total weight of the composition of at least one oil,
from 1% to 10% by weight relative to the total weight of the composition of at least one polar wax, and
at least one hydrophilic solvent chosen from the group formed of water and $C_1$-$C_5$ compounds comprising at least one OH group,
wherein
the weight ratio of the anionic surfactant of formula (I)/fatty alcohol is from 1/5 to 1/3, and
a mean haze value of a 25 μm film of the composition applied onto 50 μm polyethylene (PE) film measured according to standard ASTM D 1003 after 1 hour of drying at room temperature is at least 80%.

* * * * *